(12) United States Patent
Nishtala et al.

(10) Patent No.: US 8,137,309 B2
(45) Date of Patent: Mar. 20, 2012

(54) INDWELLING URINARY DRAINAGE CATHETER

(75) Inventors: Vasu Nishtala, Snellville, GA (US); Rex Nagao, Tokyo (JP)

(73) Assignee: C.R. Brad, Inc., Murray Hill, NJ (US)

( * ) Notice: Subject to any disclaimer, the term of this patent is extended or adjusted under 35 U.S.C. 154(b) by 328 days.

(21) Appl. No.: 11/994,484

(22) PCT Filed: Jun. 29, 2006

(86) PCT No.: PCT/US2006/025818
§ 371 (c)(1),
(2), (4) Date: Sep. 25, 2008

(87) PCT Pub. No.: WO2007/005734
PCT Pub. Date: Jan. 11, 2007

(65) Prior Publication Data
US 2009/0030370 A1 Jan. 29, 2009

Related U.S. Application Data

(60) Provisional application No. 60/695,955, filed on Jul. 1, 2005.

(51) Int. Cl.
*A61M 25/10* (2006.01)
(52) U.S. Cl. .............. 604/103.01; 604/517; 604/103.07; 604/103.04; 604/544
(58) Field of Classification Search .......... 604/516–517, 604/103.07, 103.14, 105–108, 264, 544, 604/96.01, 97.01, 530, 327–329, 103.01, 604/907–908, 912, 915–921, 540
See application file for complete search history.

(56) References Cited

U.S. PATENT DOCUMENTS

| | | | |
|---|---|---|---|
| 4,820,270 A | 4/1989 | Hardcastle et al. | |
| 4,878,495 A * | 11/1989 | Grayzel | 606/193 |
| 5,250,029 A | 10/1993 | Lin et al. | |
| 5,454,798 A | 10/1995 | Kubalak et al. | |
| 5,616,126 A | 4/1997 | Malekmehr et al. | |
| 6,096,013 A * | 8/2000 | Hakky et al. | 604/349 |
| 6,719,709 B2 | 4/2004 | Whalen et al. | |
| 6,837,868 B1 | 1/2005 | Fajnsztajn | |
| 6,893,418 B2 | 5/2005 | Liu | |
| 6,893,430 B2 | 5/2005 | Eshel et al. | |
| 6,942,641 B2 | 9/2005 | Seddon | |
| 7,264,609 B2 * | 9/2007 | Hakky et al. | 604/107 |
| 7,347,866 B2 * | 3/2008 | Daignault et al. | 606/191 |
| 7,465,286 B2 * | 12/2008 | Patterson et al. | 604/43 |
| 2002/0143292 A1 | 10/2002 | Flinchbaugh | |
| 2005/0049576 A1 | 3/2005 | Snell et al. | |
| 2009/0030370 A1 | 1/2009 | Nishtala et al. | |

OTHER PUBLICATIONS

PCT Search Report, Application No. PCT/US2006/025818, Apr. 5, 2007.

* cited by examiner

*Primary Examiner* — Quynh-Nhu H Vu
(74) *Attorney, Agent, or Firm* — Rutan & Tucker, LLP

(57) ABSTRACT

A catheter is described herein, having a catheter shaft including a proximal end and a distal end, a tip attached to the distal end, including first and second legs spaced apart to form a slot therebetween, the slot in fluid communication with a lumen of the catheter shaft, and a bladder inflatable element positioned over an outer surface of at least one of the first and second legs.

16 Claims, 12 Drawing Sheets

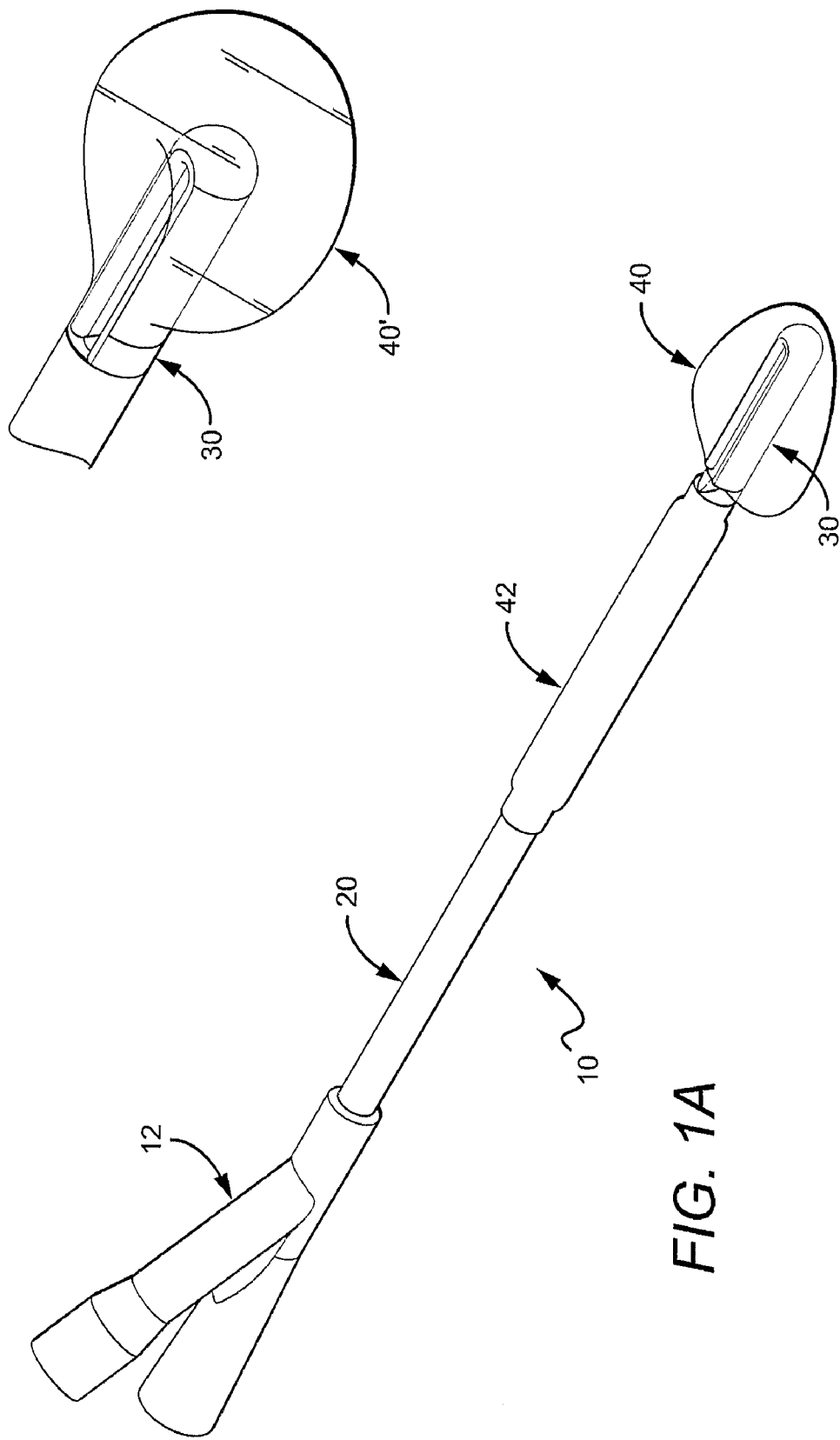

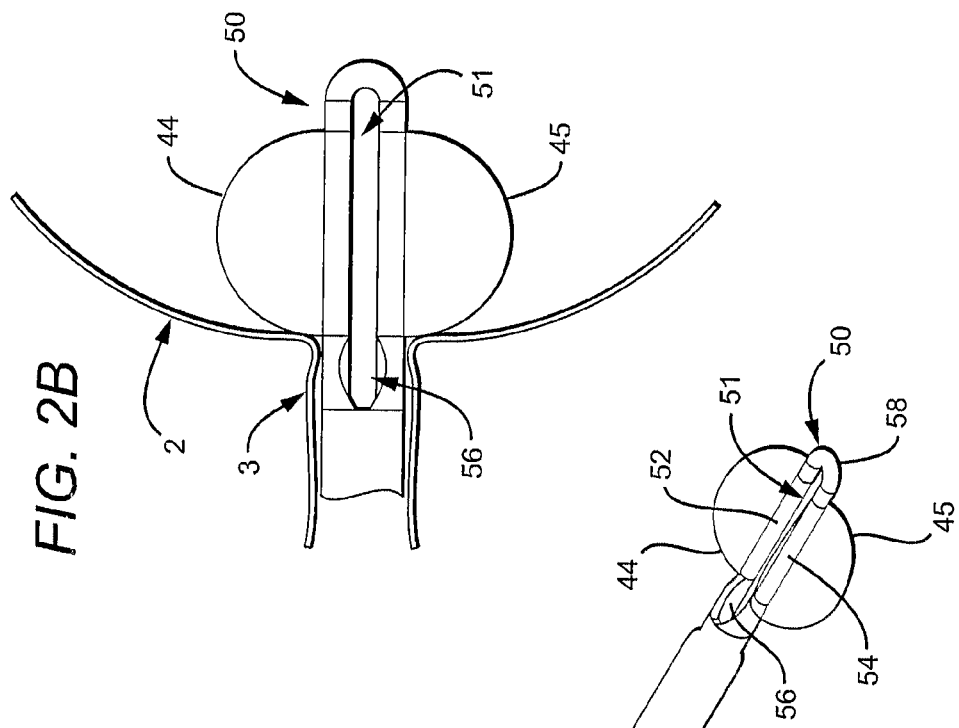
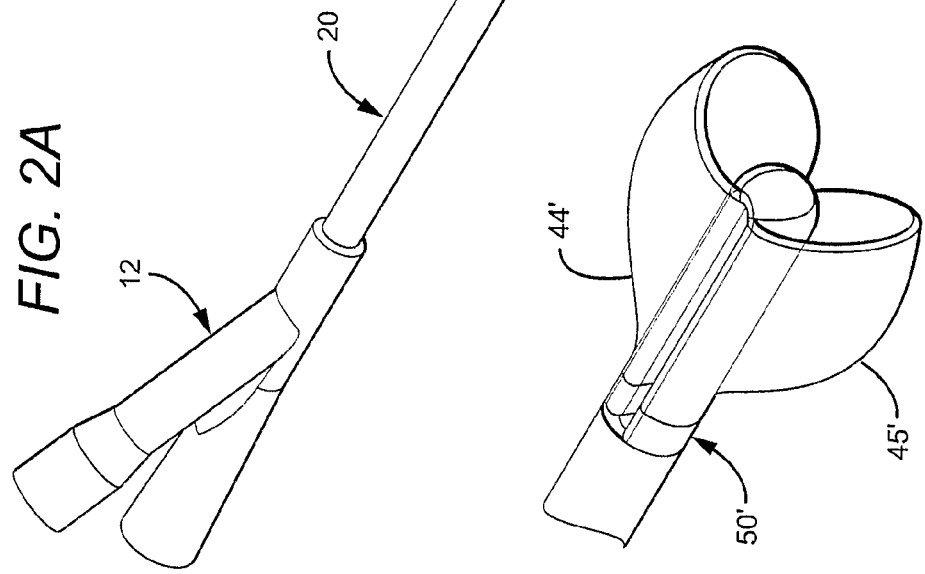

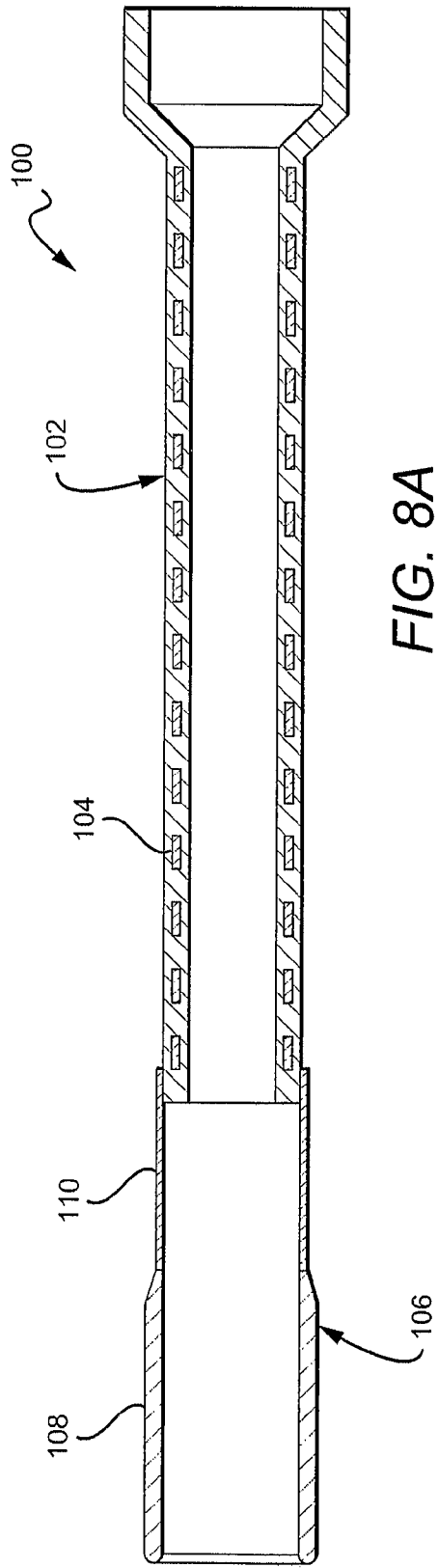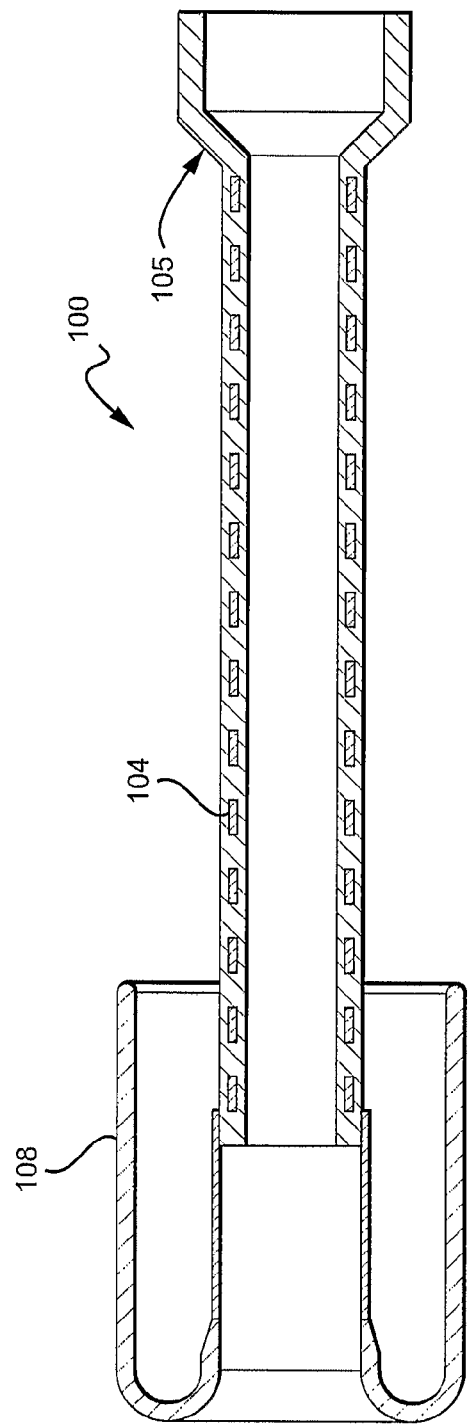

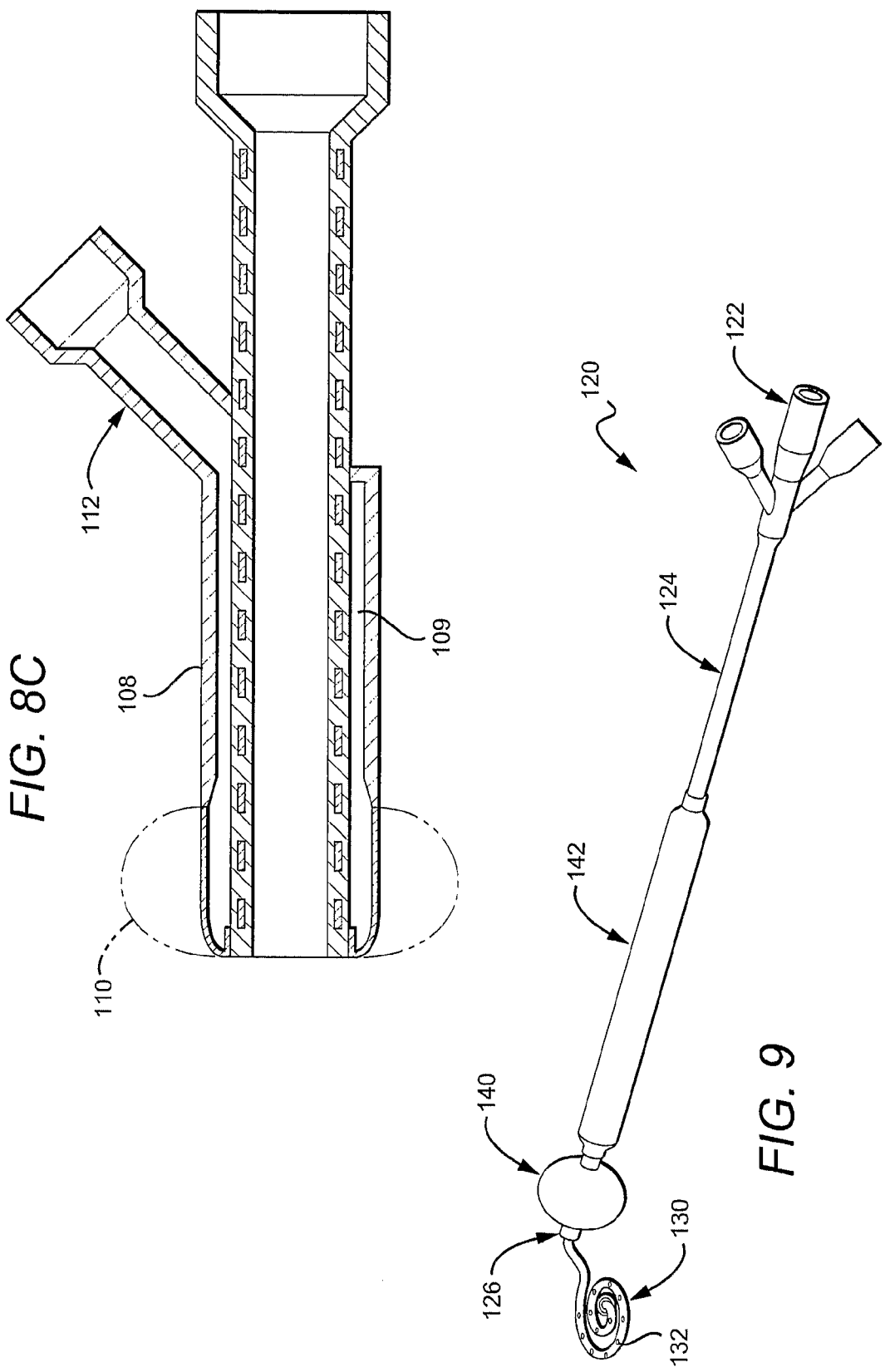

FIG. 10A
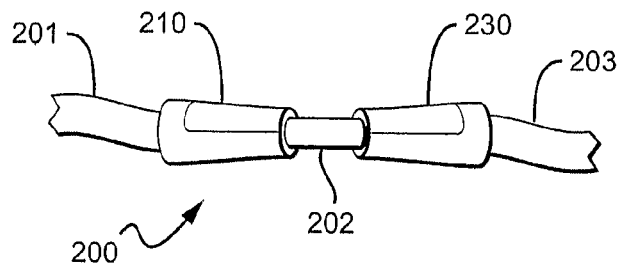
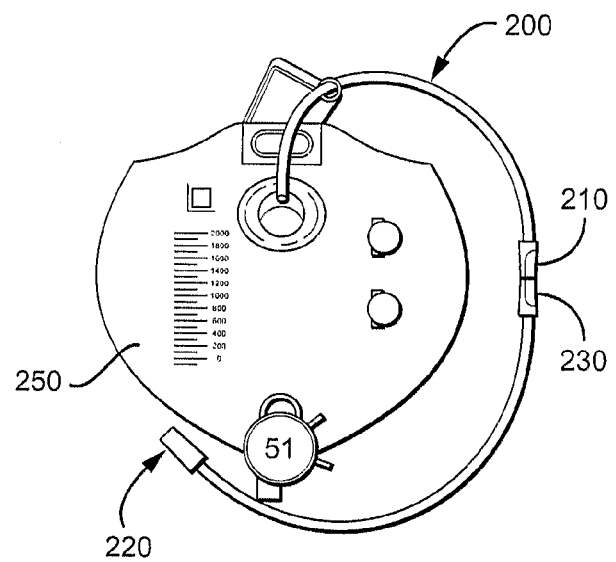
FIG. 10B
FIG. 10C
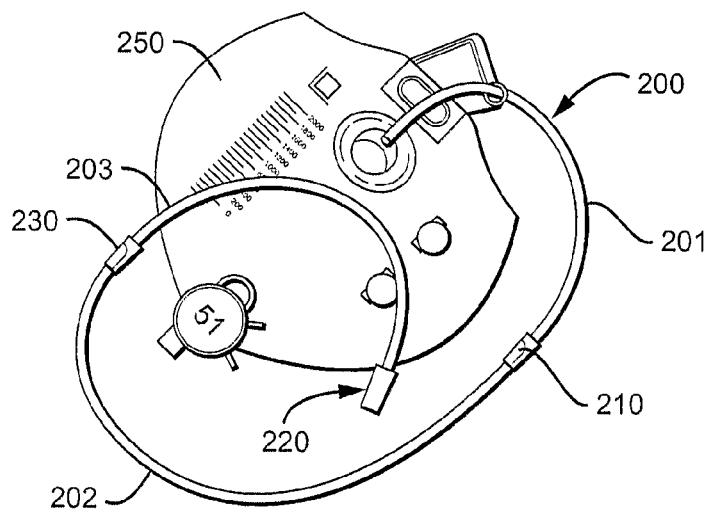

INDWELLING URINARY DRAINAGE CATHETER

PRIORITY

This application is a U.S. national stage application under 35 USC §371 of International Application No. PCT/US2006/025818, filed Jun. 29, 2006, which claims the benefit of priority, under 35 U.S.C. §119(e), to U.S. Provisional Application No. 60/695,955, filed Jul. 1, 2005, each of which is incorporated by reference into this application as if fully set forth herein.

BACKGROUND OF THE INVENTION

A standard Foley catheter design generally includes a balloon disposed at a distal end of the catheter to anchor the catheter in the bladder, the catheter including at least one lumen to drain urine from the bladder and at least one lumen to inflate the balloon (e.g., with sterile water). The proximal end of the Foley catheter includes at least two ports in communication with the two lumens, a first that is connected to the drainage lumen and has an interface with fittings for drainage and sampling and a second that is connected to the inflation lumen with a valve to ensure the inflation fluid remains within the lumen and balloon once filled. The tip of a standard Foley catheter extends beyond the sides of the balloon into the bladder and includes one or more apertures or "eyes" to drain fluids and debris from the bladder. This standard design has not changed in approximately 100 years, although catheters with various additions (e.g., mechanical anchors, etc.) and improvements have been proposed and investigated.

BRIEF SUMMARY OF THE INVENTION

Accordingly, described herein are urinary catheters including features believed to provide advantages over a standard Foley catheter. In one embodiment, a urinary catheter includes a bladder inflatable element and a urethral inflatable element, the bladder inflatable element providing an anchor for the catheter in the bladder and the urethral inflatable element providing an anchor for the catheter in the urethra. In one embodiment, the bladder inflatable element is configured as a lobe, rather than a sphere, to permit a large opening in the distal end of the catheter for passage of fluids and debris, to prevent "cuffing" upon removal of the catheter from the bladder, and to provide a soft distal end to reduce bladder spasm and enhance patient comfort. The opening in one embodiment is the area between two legs of a tip attached to the distal end of a catheter shaft. In one embodiment, the bladder inflatable element is a one lobe design, while in another embodiment, the bladder inflatable element is a two lobe design. In one embodiment of a two lobe design, the distal section thereof includes detachable legs, each having a bladder inflatable element positioned thereon. The legs are connected (e.g., mechanically, adhesively, etc.) for insertion into the bladder, but in one embodiment become detached upon inflation of the inflatable elements. Upon detachment, the legs operate similarly to a funnel to ensure full drainage of the bladder.

In one embodiment, a catheter includes a catheter shaft including a proximal end and a distal end, a tip attached to the distal end, including first and second legs spaced apart to form a slot therebetween, the slot in fluid communication with a lumen of the catheter shaft, and a bladder inflatable element positioned over an outer surface of at least one of the first and second legs.

In another embodiment, a catheter includes a catheter shaft including a proximal end and a distal end, a tip attached to the distal end of the catheter shaft, the tip including a first leg spaced apart from a second leg to form a slot therebetween, the slot in fluid communication with a lumen of the catheter shaft, the first and second legs detachably connected by an attachment mechanism, and a first bladder inflatable element positioned around a section of the first leg and a second bladder inflatable element positioned around a section of the second leg, the first and second legs detaching upon inflation of at least one of the first and second bladder inflatable elements.

In another embodiment, a catheter includes a catheter shaft including a proximal end and a distal end, an outer sleeve positioned about the catheter shaft such that an annular region is created therebetween, the sleeve including an inflatable section along a distal section thereof, and a tip attached to the distal end of the catheter shaft, the tip comprising a dissolvable material.

In another embodiment, a catheter includes a catheter shaft including a proximal end and a distal end, an outer sleeve including an inflatable member and an inflation jacket, the inflatable member attached to the distal end of the catheter shaft, the inflation jacket attached to a hub, and an annular region between the outer sleeve and the catheter shaft, the hub including a port in fluid communication with the annular region.

In another embodiment, a catheter includes a catheter shaft including a drain lumen, a bladder inflatable element disposed over a distal end of the catheter shaft, a urethral inflatable element disposed over a distal region of the catheter shaft, proximal of the bladder inflatable element, and a drain element, including a lumen and a plurality of openings along a length thereof, the drain element positioned within a distal end of the drain lumen in an insertion position and having a distal section extending from a distal opening of the drain lumen in fluid communication therewith in a deployed position.

In one embodiment, a urine drainage system includes a catheter including a catheter shaft with a drainage lumen and a tip attached to a distal end of the catheter shaft, the tip including spaced apart first and second legs forming a slot therebetween, a first bladder inflatable element positioned over an outer surface of at least one of the first and second legs, and a urine collection system including extendable tubing having a first end connected to a collection receptacle and a second end with an opening in fluid communication with the drainage lumen of the catheter shaft.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1A is a perspective view of one embodiment of a catheter including a one lobe bladder inflatable element.

FIG. 1C is a perspective view of another embodiment of a one lobe bladder inflatable element.

FIG. 2A is a perspective view of one embodiment of a catheter including a two lobe bladder inflatable element.

FIG. 2B is a perspective view of the distal end of the catheter of FIG. 2A inserted within a bladder.

FIG. 2C is a perspective view of another embodiment of a two lobe bladder inflatable element.

FIGS. 8A-C are longitudinal cross-sectional views of another embodiment of a catheter with an outer sleeve positioned over a catheter shaft, showing different stages of assembly.

FIG. 9 is a perspective view of one embodiment of a catheter with a drain element.

FIG. 10A is a perspective view of a region of an extendible tubing for a urine collection device.

FIGS. 10B and 10C show a urine collection device having extendible tubing that is contracted and extended, respectively.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1B:
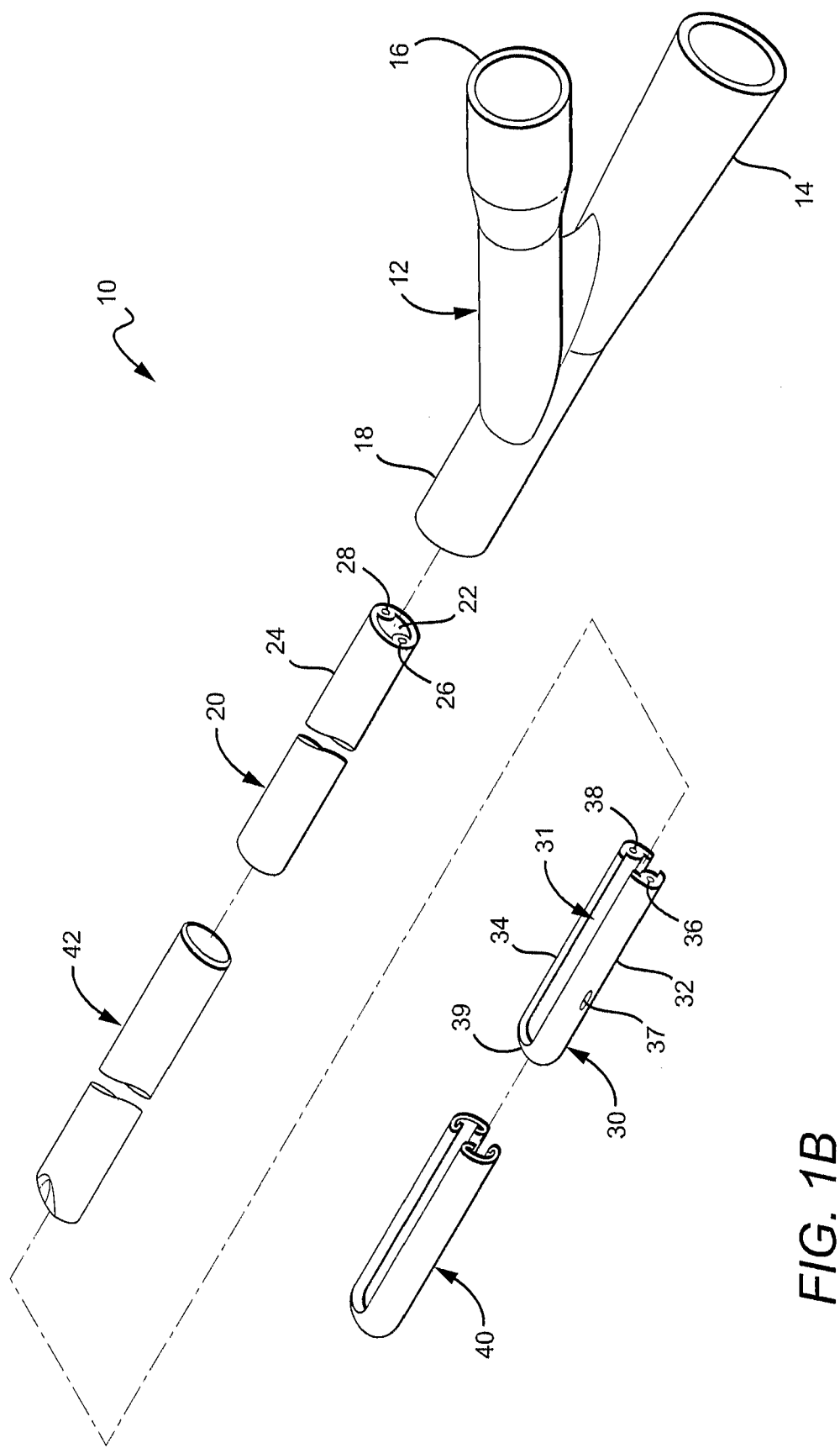
FIG. 1B is an exploded view of the catheter of FIG. 1A.

In one embodiment, efficient drainage of fluids and debris from the bladder is accomplished by maximizing the area of drainage along the entire distal end of the catheter rather than one or more small openings. This is accomplished by providing a tip with an elongated opening surrounded by a bladder inflatable element, exemplary embodiments for which are illustrated in the figures. In particular, the bladder inflatable element may be configured, for example, as a single lobe as shown in FIGS. 1A-C, as a two lobe as shown in FIGS. 2A-2C, or as a multi lobe (e.g., three lobes or more). Referring first to FIG. 1A, a urinary catheter 10 is illustrated with a catheter shaft 20 having a hub 12 attached to its proximal end and a tip 30 attached to its distal end. Surrounding the tip 30 is a bladder inflatable element (e.g., balloon) 40 and surrounding a distal region of the shaft 20 is a urethral inflatable element 42. In this view, both inflatable elements 40, 42 are shown inflated. Aspects of the urinary catheter 10 are shown in more detail in the exploded view of FIG. 1B.

The hub 12 includes a drainage port 14 and an infusion port 16, the drainage port in fluid communication with the central lumen 22 of the catheter shaft 20 and the infusion port 16 in fluid communication with the infusion lumens 26, 28 thereof. The distal end of the hub 12 includes a receiving area 18 into which a proximal end of the catheter shaft 20 is secured. As is known to one skilled in the art and as used herein, a catheter hub provides facilitates connection between a catheter and/or aspects thereof and external equipment or devices. Thus, it should be appreciated that the catheter hubs discussed herein include various connection capabilities even though not specifically called forth, such as, for example, interfaces for luer connectors or other types of medical device connectors, connections to external drainage tubing, connections to devices configured to deliver inflatable elements (e.g., fluid, gas, etc.) under pressure, etc.

Connected to the distal end of the catheter shaft 20 is a catheter tip 30, which includes two legs 32, 34 that are connected at a distal end by a connecting member 39, forming a loop-like structure, the legs 32, 34 including lumens 36, 38, respectively, for inflation of the bladder inflatable element 40 and having inflation apertures 37, 39 to provide fluid communication between the lumens 36, 38 and the bladder inflatable element 40 positioned therearound. The lumens 36, 38 are in fluid communication with infusion lumens 26, 28 of the catheter shaft 20 when the tip 30 is connected thereto. The two legs 32, 34 are spaced apart such that a slotted region or slot 31 is formed, which is in fluid communication with the central lumen 22 of the catheter shaft 20 to enable drainage of fluid from the bladder of a patient. As used herein, the terms slot, slotted region, eye opening, opening, etc. are used interchangeably to indicate a space between legs of a catheter tip. The bladder inflatable element 40, which in one embodiment is made of an elastomeric material, is shaped similarly to the catheter tip 30 and is positioned therearound such that, in the case of the one lobe design shown in FIGS. 1A and 1B, each leg 32, 34 of the catheter tip 30 has attached to it a portion of the bladder inflatable element 40 (i.e., as seen in the embodiments shown in FIGS. 1A and 1B, the one lobe design for the bladder inflatable element 40 includes a non-spherical inflatable element around the tip of the catheter such that no non-inflatable catheter element can come in contact with portions of the bladder). Likewise, the urethral inflatable element 42 is shaped similarly to the catheter shaft 20 and is positioned therearound. FIG. 1C illustrates another embodiment of the one lobe design, in which a bladder inflatable element 40' is expandable to a greater size than bladder inflatable element 40, illustrating an extent beyond the legs 32, 34 of the tip 30 that the inflatable element can be expanded. In other embodiments, the bladder inflatable element may have the capacity for more or less expansion.

Compared to a standard spherical balloon on a Foley catheter that may not completely prevent post residual void volumes due to the accumulated pooling of urine near the bladder neck, the one lobe and two lobe designs described herein enable substantially complete drainage from the bladder of a patient as the eye opening or slotted region 31 extends to the bladder neck (i.e., the proximal end of the opening or slotted region 31 between the legs 32, 34 of the tip 30 resides within the neck of the bladder when the catheter tip 30 is properly positioned in the bladder of a patient and the bladder inflatable element(s) 40 are inflated, see, e.g., FIG. 2B). Also, the larger opening provided by the slotted region 31 between the legs 32, 24 of the tip 30 permits passage of clots, sand, stones and other debris that may not be able to pass through an opening in a standard Foley catheter. Moreover, the absence of a non-inflatable catheter tip element in the one lobe design minimizes the impact on the trigone area, which should enhance patient comfort and reduce bladder spasm. Further, as the bladder inflatable element 40 stretches with time, there is no "cuffing" issue (standard bladder balloon stretched portion creates larger profile for catheter tip, making withdrawal difficult and/or uncomfortable) common to standard Foley catheters because any stretched portion of the balloon advances to the distal end of the catheter, which does not increase the catheter tip profile as the catheter is withdrawal from the patient.

FIG. 2A illustrates a two lobe design of the bladder inflatable element in more detail, with the catheter shaft 20 and the hub 12 of FIG. 1A. In the two lobe design, legs 52, 54 of tip 50 have attached respectively thereto separate bladder inflatable elements 44, 45 (shown inflated). The tip 50 includes a slotted region 51 positioned between the legs 52, 54, which are connected at a distal end by connecting member 58, and which are connected at a proximal end to catheter shaft 20 such that inflation lumens 26, 28 of catheter shaft 20 are in fluid communication with respective lumens in legs 52, 54. The legs 52, 54 include an opening in a side thereof to place the lumens in fluid communication with the bladder inflatable elements 44, 45. The tip 50 includes an expanded region 56 adjacent a proximal end thereof to potentially enhance drainage from the bladder. The connecting member 58 of catheter tip 50 in this embodiment, is not completely surrounded by the bladder inflatable elements 44, 45, unlike the one lobe design, which may structurally offer increased stiffness for insertion of the tip 50 into the patient.

Referring to FIG. 2B, an outline of a bladder 2 is shown to demonstrate how the tip 50 is positioned with respect to the bladder 2 with the expanded region 56 residing in the bladder neck 3, thereby facilitating drainage therefrom. FIG. 2C illustrates another embodiment of the two lobe design, in which the bladder inflatable elements 44', 45' extend distally further on the tip 50' (which in this embodiment does not include expanded region 56) and also have ends that are positioned at an angle with respect to a longitudinal axis of the catheter shaft 20. It should be appreciated that there are other possibilities for the shape of the inflatable element(s), as well as the different configurations possible depending on attachment points of the inflatable element(s) to the catheter tip, all of which are within the scope of the invention. Also, although the catheter shaft 20 in the embodiments in FIGS. 2A-C is shown without a urethral inflatable element (e.g., balloon), it is an optional feature that could be incorporated therein.

Figure 3A:
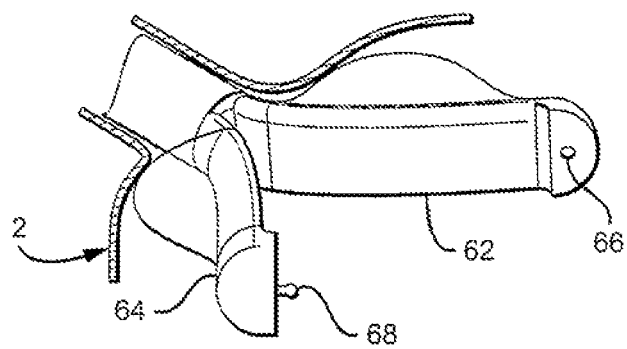
FIG. 3A is a perspective view of one embodiment of a separable tip shown in an insertion configuration.
Figure 3B:
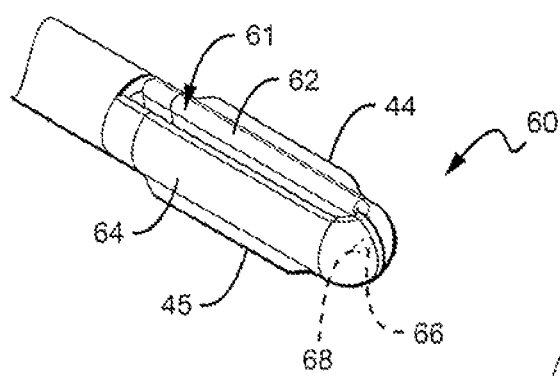
FIG. 3B is a perspective view of the tip of FIG. 3B shown following inflation of the bladder inflatable elements.
Figure 4:
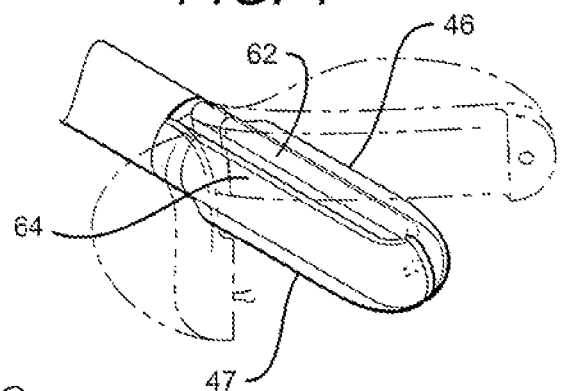
FIG. 4 is a perspective view of another embodiment of a separable tip.

FIGS. 3A-3B illustrate another embodiment of a two lobe design. In this embodiment, two separate bladder inflatable elements 44, 45 are attached to opposing legs 62, 64 of catheter tip 60. Whereas in the previously illustrated embodiments of the two lobe design, the legs are permanently joined at a distal end by a connecting member, in this embodiment the legs 62, 64 are detachable, connected by an attachment mechanism. As shown in FIG. 3A, the legs 62, 64 of the catheter tip 60 are connected mechanically, in which leg 64 includes one or more protrusions 68 that are received in one or more indentations or recessions 66 in leg 62 in an interference fit arrangement. Prior to insertion, the legs 62, 64 are "snapped" together or otherwise attached to one another, but after insertion into the bladder 2 and upon inflation of the bladder inflatable elements 44, 45, the legs separate to provide a wide opening or funnel-type configuration to facilitate urinary drainage as shown in FIG. 3B. The space between the legs, or slotted region 61, includes a proximal end that extends into the neck of the bladder 2, permitting substantially complete bladder drainage and preventing residual pooling of urine. In another embodiments the attachment mechanism includes an adhesive that, for example, either dissolves in the presence of urine or is made of a material of sufficiently low-force to permit separation of the legs upon insertion into the bladder and inflation of the bladder inflatable elements. FIG. 4 illustrates another embodiment of a two-lobe design with separable legs, in which bladder inflatable elements 46, 47 extend over the distal ends of the legs 62, 64 to maximize patient comfort. As shown in phantom, upon inflation of the bladder inflatable elements 46, 47 the legs 62, 64 separate and form the funnel-type configuration shown in FIG. 3B.

Figure 5A:
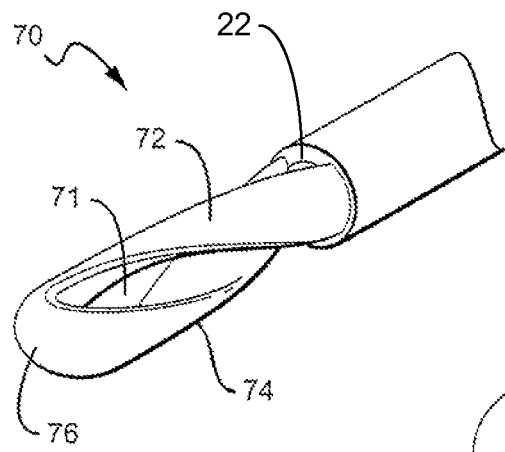
FIG. 5A is a perspective view of another embodiment of a catheter tip.
Figure 5B:
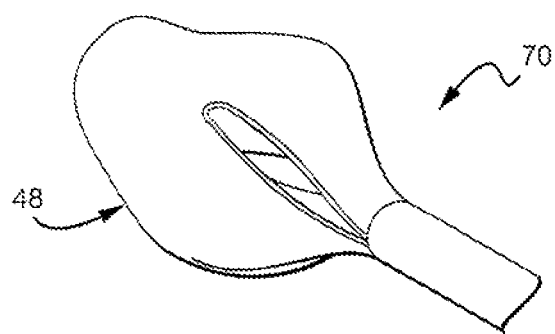
FIG. 5B is a perspective view of the catheter tip of FIG. 5A with a bladder inflatable element attached thereto.
Figure 5C:
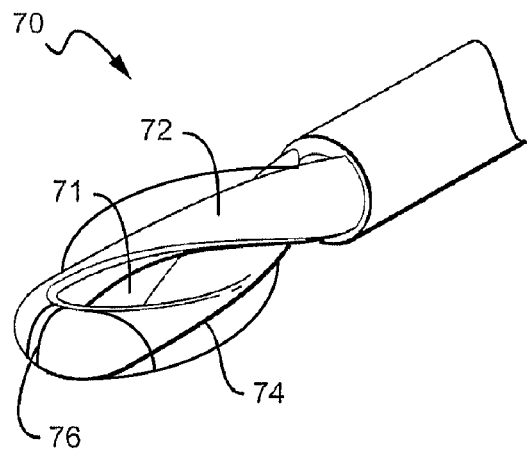
FIG. 5C is a view of the catheter tip including a multi lobe design.
Figure 5D:
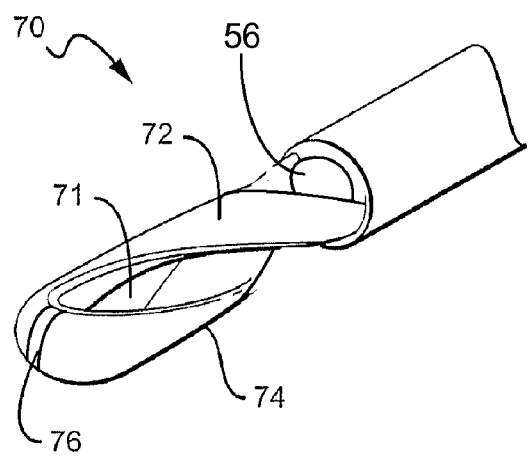
FIG. 5D is a view of another example catheter tip including an expanded region.
Figure 5E:
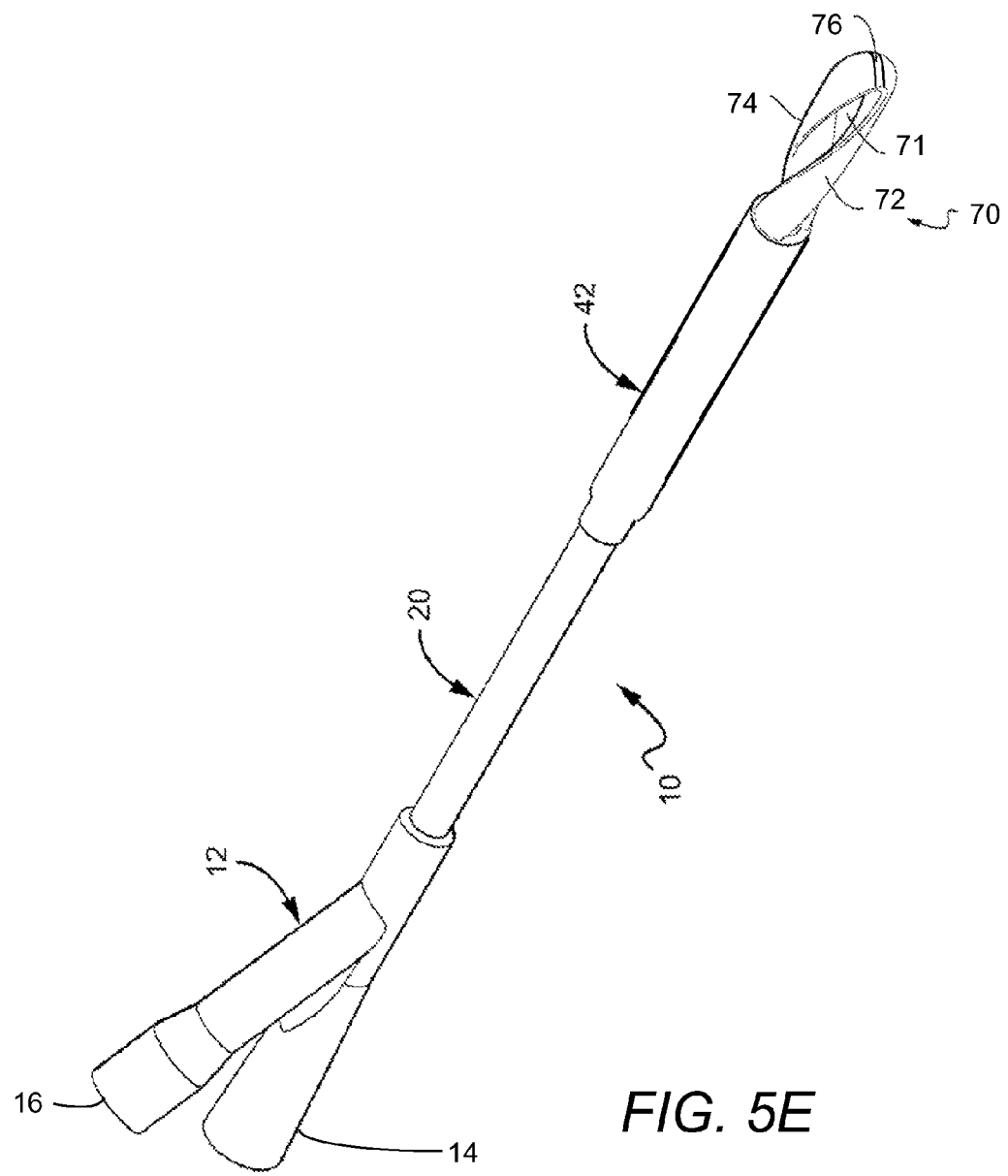
FIG. 5E is a perspective view of one embodiment of a catheter in accordance with the systems and methods described herein.

FIG. 5A shows another embodiment of a catheter tip for use in a one lobe, e.g., FIGS. 1A-C, or multi lobe, e.g., FIGS. 2A-C, design. It will be understood by those of skill in the art that catheter tip 70 may be used, for example, in place of catheter tip 30 of FIGS. 1A-C or tip 50 of FIGS. 2A-C. Catheter tip 70 includes legs 72, 74 connected by a connecting member 76, the legs 72, 74 twisted out of plane such that the opening or slotted region 71 is helical in shape and is therefore simultaneously open to many different areas of the bladder, a configuration which is believed to assist in drainage therefrom. FIG. 5B shows tip 70 with a one lobe bladder inflatable element 48 attached thereto, although as mentioned, a two lobe, three lobe or other multi lobe design could also be attached as illustrated in FIG. 5C. The catheter tip 70 may also include an expanded region 56 as illustrated in FIG. 5D. FIG. 5E illustrates a perspective view of one embodiment including catheter tip 70 attached to shaft 20.

Referring back to FIG. 1A, an optional urethral inflatable element 42 is shown positioned around the catheter shaft 20 proximal to the bladder inflatable element 40. This feature, in one aspect, acts as a urethral tamponade to ensure that urine does not leak near the bladder neck. The urethral inflatable element 42 is believed to provide several benefits. For instance, migration of extra luminal bacteria around the catheter is believed to be minimized, sizing difficulties are overcome in that the urethral balloon provides a one size fits all capability to the catheter, and because the urethral balloon immobilizes the catheter upon inflation, thereby sealing the catheter within the urethra, a pistoning effect of the catheter (i.e., movement of the catheter shaft in both proximal and distal directions while the catheter is implanted) is prevented and the level of anchor strength required of the bladder inflatable element reduced, providing patient comfort and making size and shape of the catheter for different patients less critical. In addition, the material of the urethral inflatable element 42 may be made softer than the surface of the catheter shaft 20 to enhance patient comfort.

Figure 6A:
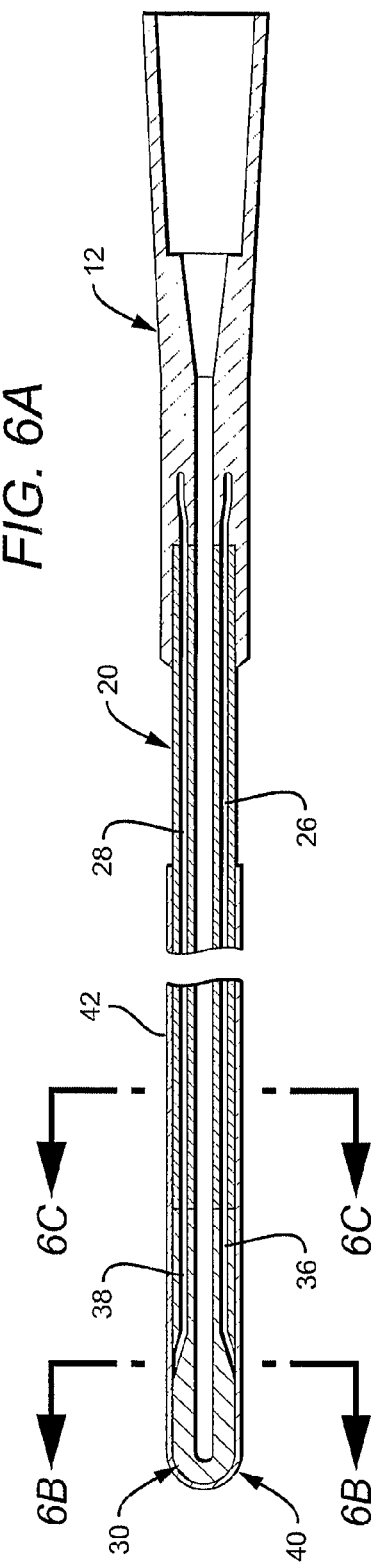
FIG. 6A is a longitudinal cross-sectional view of the catheter of FIG. 1A.
Figure 6C:
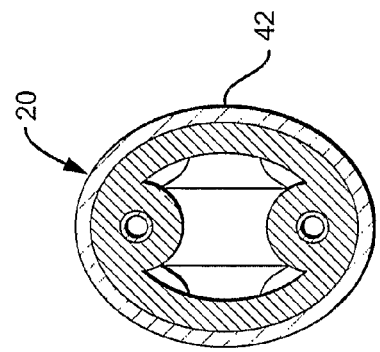
FIG. 6C is a cross-sectional view of the catheter of FIG. 6A along section C-C.
Figure 6B:
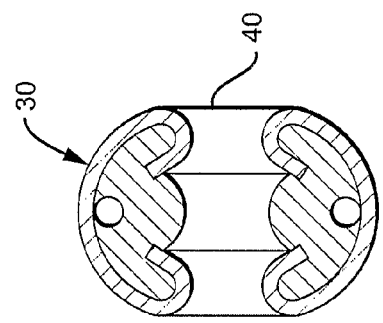
FIG. 6B is a cross-sectional view of the catheter of FIG. 6A along section B-B.

FIG. 6A shows a cross-sectional view of the urethral catheter 10 prior to inflation of the inflatable elements 40, 42. The inflation lumens 26, 28 of catheter shaft 20 are seen in this view having a distal end in fluid communication, respectively, with lumens 36, 38 of the tip 30. The inflation lumens 26, 28 are connected at the proximal end to poll 16 of hub 12. In this embodiment, the inflation lumens 26, 28 are utilized to inflate both the urethral inflatable element 42 and the bladder inflatable element 40 through a connection to a single inflation source connected to the hub 12 (and in particular to the port 16). In other embodiments, the inflation lumens 26, 28 are connected to separate inflation systems/ports in the hub 12. In one variation, the urethral inflatable element 42 is in fluid communication with a different inflation source than the bladder inflatable element 40. One potential inflation fluid for the urethral inflatable element in such a system is an active inclusion compound agent, such as an antimicrobial compound (e.g., as chlorhexidine) to aid in infection control or an antithrombogenic compound to achieve hemostasis in urologic surgery, which in one embodiment diffuses through the balloon and into the urethra. In the cross-sectional views of FIGS. 6B and 6C, the elliptical shape of the catheter shaft 20 and tip 30 can be seen, which closely resembles the shape of the urethra. As shown in FIGS. 6A and 6B, the lumens 36, 38 branch toward the outer wall of the respective legs 32, 34 of the tip 30 to communicate with openings 37, 39 (FIG. 1B).

Figure 7:
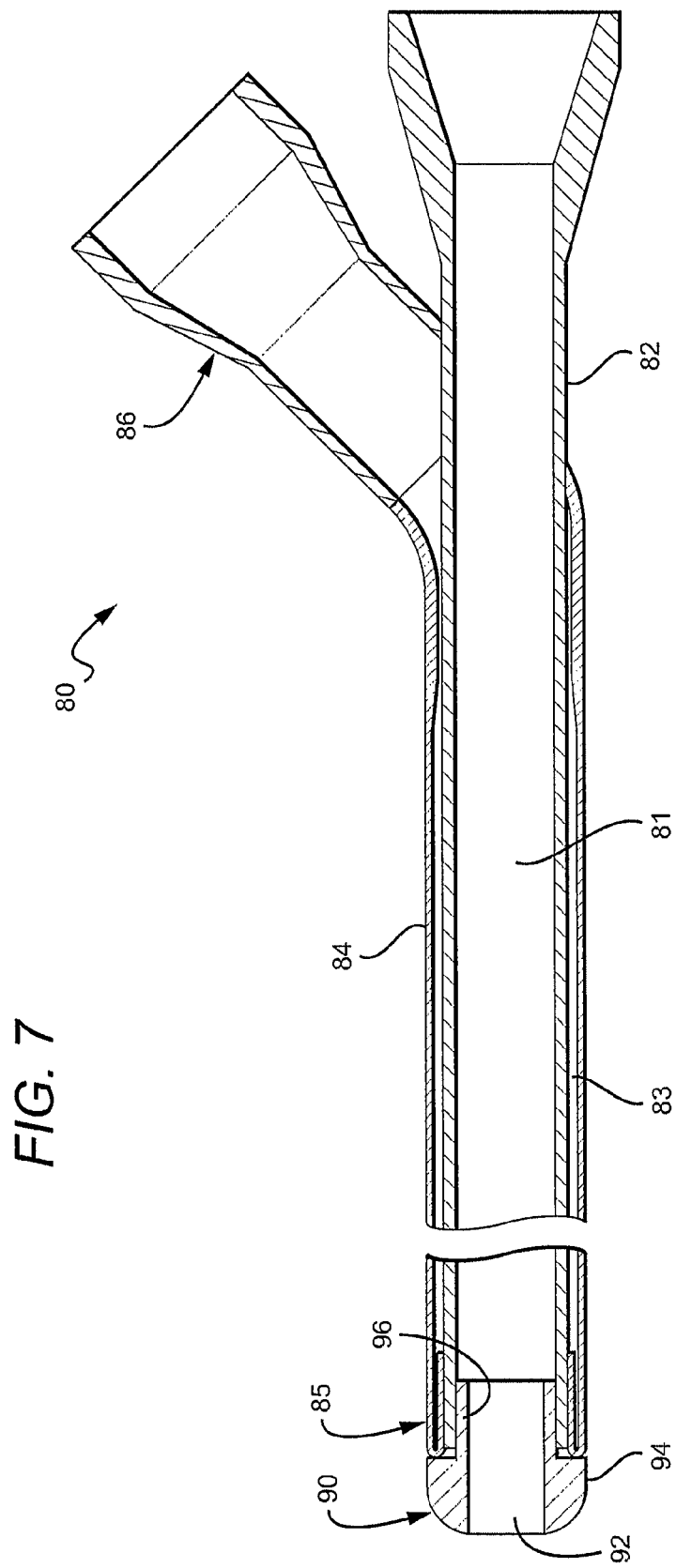
FIG. 7 is a longitudinal cross-sectional view of one embodiment of a catheter with an outer sleeve positioned over a catheter shaft.

FIG. 7 illustrates another embodiment of a urinary catheters. In this embodiment, a catheter 80 includes an inner luminal shaft 82 for drainage and an outer sleeve 84 that is inflatable, providing anchoring functionality. The inflatable outer sleeve 84 in one embodiment is a configured as a single bladder inflatable element, while in another embodiment is configured as both a bladder inflatable element and urethral inflatable element. The section that is intended to be inflated may simply be fashioned thinner than other sections of the sleeve 84 such that the thinner section (e.g., adjacent the distal end of the catheter 80) inflates upon the presence of internal pressure, whereas the remainder of the sleeve (e.g., the section proximal of the thinner section) remains closely adhered to the shaft 82. Alternatively, an inflatable element is attached on one end to the distal end of the shaft and on the other end to an inflation jacket (see FIGS. 8A-C). The feature of an inflatable outer sleeve provides a low to zero transition region between the catheter shaft and inflatable element, facilitating insertion and removal due to the resulting low profile of the catheter. The catheter 80 includes a hub 86 with dual ports 87, 89, the first port 87 connected to the shaft 82 to enable drainage from the lumen 81 thereof and the second port 89 connected to the outer sleeve 84 for delivery of an inflation element (e.g., fluid, air, etc.).

As shown in FIG. 7, the catheter 80 includes a tip 90, which in one embodiment is a dissolvable element, such as poly (glycolic acid) (PGA), (poly)ethylene glycol (PEG), etc., that is rigid at the point of introduction, but which quickly dissolves upon exposure to urine in the bladder. The tip 90 has a rounded, atraumatic outer surface 94, having a diameter substantially the same as the outer diameter of the shaft 82 plus the sleeve 84, and a stem 96 that is configured for insertion into the lumen 81. The tip 90 also, includes a lumen 92 in fluid communication with the lumen 81 of the shaft 82. The tip 90 may be friction fit inside the shaft 82 or many be bonded thereto with a dissolvable bonding agent, may be ultrasonically welded, or may be bonded with any other well-known bonding method. One advantage of a dissolvable tip, such as tip 90, is that a drainage lumen opening is always maintained directly in the path of the urine pool. Catheter 80 provides a smooth, even outer surface that is atraumatic upon both insertion and removal from a patient. In an embodiment utilizing thermoplastic materials, the outer sleeve 84 has a distal end 85 that is folded over and welded or bonded to the shaft 82 to facilitate manufacturing. The annular space between the shaft 82 and sleeve 84 acts as an inflation lumen 83, which is maximized to produce rapid rates of inflation and deflation of the inflatable section. The composite construction of catheter 80 also permits variation of stiffness through material selection, meaning that the stiffness (e.g., soft, flexible, semi-rigid, etc.) and bending properties of the catheter 80 can be adjusted according to patient need.

FIGS. 8A-C illustrate different stages of another embodiment of a urinary catheter with a shaft and outer sleeve. As shown in one stage in FIG. 8A, catheter 100 includes a catheter shaft 102 that is reinforced (e.g., a wire component embedded in the catheter shaft, etc.) to prevent deformation. As shown, the reinforcement is provided by a stainless steel coil 104, although other materials are possible, such as plastic, shape memory alloys, etc. In one embodiment, the reinforcement of the shaft is provided by a material, such as Nitinol, that imparts radial strength to the shaft to permit insertion without lumen collapse, but is soft and flexible after insertion (e.g., due to changing of properties due to temperature) to enhance patient comfort. Further reinforcement may be provided by way of a plastic stylet that resides in the drainage shaft lumen for insertion of the catheter into a patient.

Attached to the distal end of the shaft 102 is an outer sleeve 106, including an inflation jacket 108 and an inflatable member (e.g., balloon) 110. The inflatable member 110 section of the outer sleeve 106 is attached directly to the distal end of the catheter shaft 102 utilizing bonding techniques known to one skilled in the art (e.g., solvent bonding, use of adhesives, etc.). FIG. 5B shows the outer sleeve 106 rolled/folded on top of itself so that the inflation jacket 108 extends toward the proximal end 105 of the catheter shaft 102, which is shown in this embodiment engaging to a greater diameter, although in other embodiments, the catheter shaft 102 has a substantially continuous diameter along its length. An annular region 109 is created between the inflation jacket 108 and the shaft 102 for the transport of an inflation element via hub 112 to the inflatable element 110 at the distal end of the catheter 100. FIG. 5C shows the inflation jacket 108 connected to a hub 112, which in one embodiment is insert molded to the inflation jacket 108. The dashed line shows the inflatable element 110 in its inflated/expanded state while the inflation jacket 108 remains closely situated against the shaft 102. As discussed above, the absence of a non-inflatable catheter tip element minimizes the impact on the trigone area, which should enhance patient comfort and reduce bladder spasm.

Figure 8D:
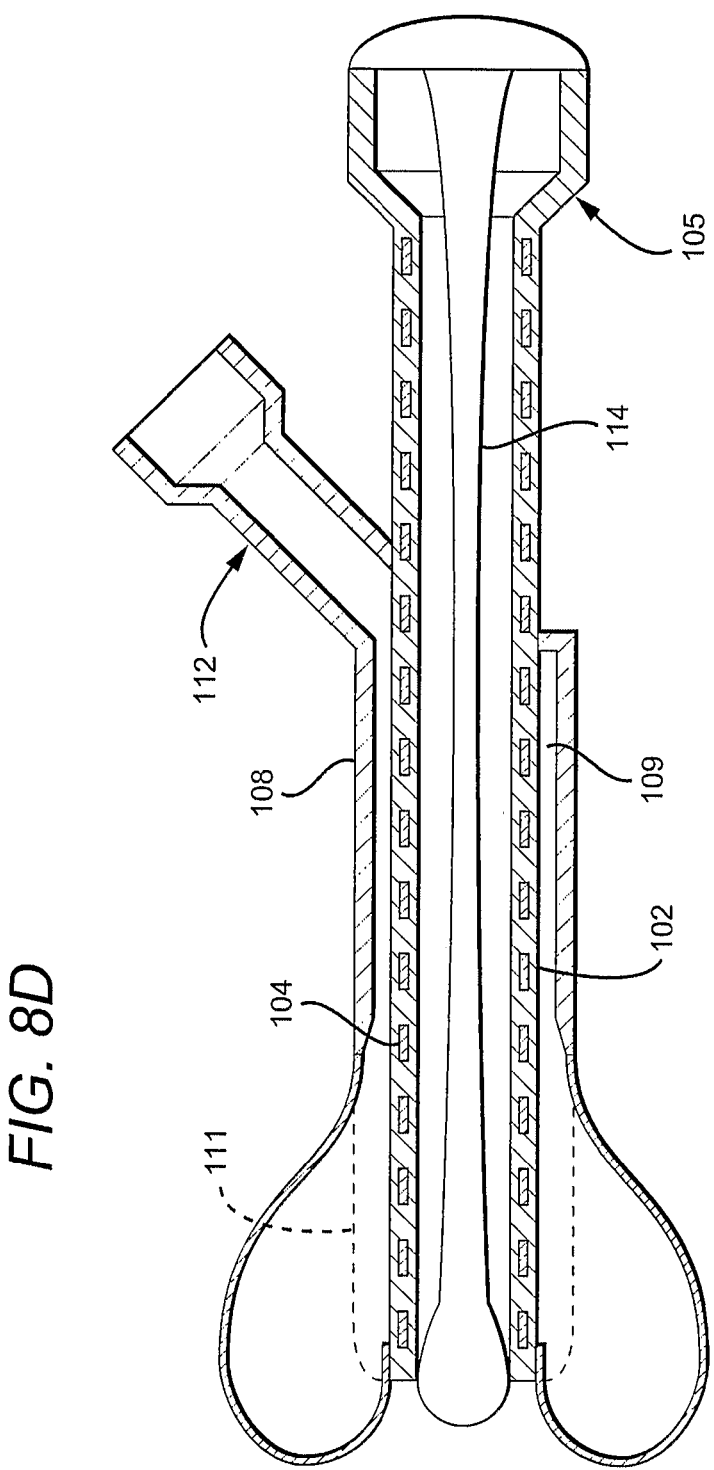
FIG. 8D is a longitudinal cross-sectional views of another embodiment of a catheter with an outer sleeve positioned over a catheter shaft.

FIG. 8D illustrates an embodiment of a urinary catheter having an inflatable element 111 with a slightly different shape than inflatable element 110. Catheter 101 includes a catheter shaft 102 with a reinforcement element 104 embedded therein, an insertion stylet 114 shown inserted into a lumen of the shaft 102. An inflatable element 111 attached to a distal end of the catheter 101 has a heart shape in cross-section when inflated, but is closely situated against the catheter shaft during insertion (shown by dashed lines). Catheters 100 and 101 are believed to provide advantages with respect to, for example, maximizing drainage, facilitation of manufacturing (e.g., no tip design necessary, fewer parts, etc.), ease of insertion and prevention of lumen collapse due to axial stiffness of catheter shaft, enhanced patient comfort (e.g., tipless design, flexible shaft, etc.), faster inflation and deflation times, etc. Moreover, because the inflation jacket 108 extends to the proximal end of the catheter shaft, there is no transition region along the length of the catheter, which facilitates insertion and removal and enhances patient comfort.

FIG. 9 illustrates another embodiment of a urinary catheter 120 that includes both a bladder inflatable element 140 and a urethral inflatable element 142, although in other embodiments, only a bladder inflatable element is provided. Catheter 120 features the use of a drain element 130 extending from a distal end thereof in a deployed position such that it lies within a urine pool of a compressed bladder when the catheter 120 is properly inserted. The drain element 130 in one embodiment is a flexible or floppy tubular conduit with a plurality of openings 132 along its length that assumes a coiled shape, permitting more complete and efficient drainage of urine from the bladder as it conforms to the three-dimensional geometry thereof. The soft flexible nature of the drain element 130 provides patient comfort and minimizes bladder spasm. Any number of openings 132 and pattern thereof along the drain element 130 are contemplated herein. The drain element 130 has a proximal end inserted into a central lumen of the catheter shaft 124 and bonded thereto by methods known to one skilled in the art. When the catheter 120 is inserted into a bladder of a patient, the drain element 130 is initially contained within the central lumen of the catheter shaft 124 (i.e., the drain element 130 is in an insertion position). The drain element 130 may be deployed within the bladder by sending pressurized gas (e.g., air) through the central lumen of the catheter shaft 124.

The bladder inflatable element 140 and urethral inflatable element 142 are shown in an inflated/expanded state to illustrate the gaps therebetween and between the distal end of the bladder inflatable element 140 and the distal end 126 of the shaft 124. In other embodiments, however, the bladder inflatable element 140 covers substantially the length of the distal end 126 such that very small gaps or no gaps at all are present between the bladder inflatable element 140 and the urethral inflatable element 142 and/or between the bladder inflatable element 140 and the distal tip of the shaft 124. The catheter shaft 124 is connected at its proximal end to a hub 122, which contains three ports, one that is fluidly connected to the central lumen of the catheter shaft 124 for drainage of urine and two that are separately connected to inflation lumens in the wall of the catheter shaft that are in fluid communication with the inflatable elements 140, 142. That is, differently than embodiments described above, catheter shaft 124 includes a dedicated lumen for each inflatable element.

The catheter embodiments discussed herein can be combined with the drainage and collection systems disclosed in U.S. patent application Ser. No. 11/175,578 ("the '578 application"), filed Jul. 5, 2005, which is incorporated by reference into this application as if fully set forth herein. For example, catheters configured to reduce or eliminate residual urine and debris in the bladder, such as catheters including a tip with a slotted region, can be combined with an extendible tubing system of the '578 application to provide an enhanced drainage system that permits passage of large debris, such as urine slugs, such that hydrostatic lock of the tubing is prevented.

Specifically, as shown in FIGS. 10A to 10C, one embodiment includes extendable tubing 200 having three telescoping segments forming the outer surface. In FIG. 10A, the junctions of all three segments of the extendable tubing are shown, illustrating an extendable tubing in a compressed configuration. The first segment of the outer surface 201 is connected to a first slider 210 at one end and the second segment 202 slides through the slider 210 so that at least a portion of the second segment 202 slides within the lumen of the first segment 201. Similarly, the third segment 203 of the outer surface is attached to a second slider 230 through which the second segment 202 slides. Thus, the extendable tubing may be lengthened or shortened by telescoping the first and second and second and third segments with respect to each other to select a length for the tubing. FIGS. 10B and 10C show examples of urine collection devices having extendable tubing as shown in FIG. 10A. In FIG. 10B, the extendable tubing 200 is shown in the fully compressed length. Both sliders 210, 220 abut each other, and the second segment 202 is completely within the first 201 and third 203 segments and the sliders. In FIG. 10C, the extendable tubing 200 is in the fully elongated configuration. The second segment 202 is no longer completely within the first 201 and third 203 segments, and the second segment 202 is connected to the sliders 210, 230 linking the second segment to the first and third segments.

The extendable tubing 200 has a proximal end attached to a collection receptacle 250 and a distal end that includes a connection member 220 for connecting to a hub, such as hub 12.

It may be necessary for a health care provider to manipulate the tubing by, for example, sliding one segment relative to another. This may be done in order to transit slugs of urine through the tubing and into a collection receptacle. According to some variations, at least a portion of the tubing is covered by a banner. For example, the tubing that is handled by a health care provider may be covered by a collapsible sleeve, the ends of which are fixed at the at proximate and distal ends of the tubing. Such a sleeve may be constructed of any material that is collapsible and at least partially transparent. For example, the sleeve may be constructed of polyethylene, polypropylene, or any other material known to those of ordinary skill in the art.

An enhanced drainage system is therefore provided herein. In one embodiment, the catheter shown in FIGS. 2A-2B is inserted into a patient, with the tip 50 inserted into the bladder and the expanded region 56 positioned in the bladder neck. The distal end fitting 220 of the extendable tubing 200, having been connected to drainage port 14 of hub 12 (FIG. 1B), permits fluid communication between the central lumen 22 and the collection receptacle 250 so that substantially complete drainage of the bladder is realized.

This invention has been described and specific examples of the invention have been portrayed. Wile the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the invention is found in the claims, it is the intent that this patent will cover those variations as well.

What is claimed as new and desired to be protected by Letters Patent of the United States is:

1. A catheter comprising:
    a catheter shaft including a proximal end and a distal end;
    a tip attached to the distal end, including first and second legs spaced apart to form a slot therebetween, the slot in fluid communication with a lumen of the catheter shaft; and a bladder inflatable element positioned over an outer surface of at least one of the first and second legs; wherein the legs of the tip are twisted such that the slot has a helical shape.

2. The catheter according to claim 1, further comprising a urethral inflatable element positioned over an outer surface of the catheter shaft along a distal section thereof.

3. The catheter according to claim 2, wherein the urethral inflatable element is porous to permit diffusion of an inflation fluid therethrough.

4. The catheter according to claim 3, wherein the inflation fluid comprises chlorhexidine.

5. The catheter according to claim 3, wherein the inflation fluid is selected from the group consisting of an antimicrobial compound and an antithrombogenic compound.

6. The catheter according to claim 1, wherein the bladder inflatable element is a continuous element positioned around substantially the entire outer surface of the tip.

7. The catheter according to claim 6, wherein the bladder inflatable element is non-spherical in shape.

8. The catheter according to claim 1, wherein the bladder inflatable element comprises first and second lobes, the first lobe positioned over at least a section of the first leg and the second lobe positioned over at least a section of the second leg.

9. The catheter according to claim 1, wherein the catheter shaft and tip have an elliptical cross-sectional shape.

10. The catheter according to claim 1, wherein a proximal portion of the slot resides in a bladder neck of a patient when the tip is positioned in a bladder of the patient and the bladder inflatable element is inflated.

11. The catheter according to claim 10, wherein the proximal portion of the slot has a width greater than a width of the slot positioned in the bladder of the patient.

12. The catheter according to claim 1, wherein the size and shape of the bladder inflatable element is determined by attachment points to the tip.

13. The catheter according to claim 1, wherein the legs of the tip are connected at a distal end thereof by a connecting member such that the tip is maintained in the form of a loop.

14. The catheter according to claim 1, wherein the catheter shaft and tip have an elliptical shape.

15. The catheter according to claim 1, further comprising a hub attached to the proximal end of the catheter shaft, the hub including a drainage port in fluid communication with the catheter shaft lumen and an infusion port in fluid communication with at least one infusion lumen in the catheter shaft.

16. The catheter according to claim 15, further comprising a second infusion lumen in the catheter shaft.

* * * * *